(12) United States Patent
Martin et al.

(10) Patent No.: US 10,136,982 B2
(45) Date of Patent: *Nov. 27, 2018

(54) POLYHYDROXYALKANOATE MEDICAL TEXTILES AND FIBERS

(71) Applicant: Tepha, Inc., Lexington, MA (US)

(72) Inventors: David P. Martin, Arlington, MA (US); Said Rizk, Windham, NH (US); Ajay Ahuja, Needham, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/276,693

(22) Filed: May 13, 2014

(65) Prior Publication Data

US 2014/0248331 A1   Sep. 4, 2014

Related U.S. Application Data

(62) Division of application No. 13/228,056, filed on Sep. 8, 2011, now Pat. No. 9,125,719, which is a division
(Continued)

(51) Int. Cl.
*A61L 27/48* (2006.01)
*A61F 2/00* (2006.01)
(Continued)

(52) U.S. Cl.
CPC .......... *A61F 2/0063* (2013.01); *A61L 27/18* (2013.01); *A61L 27/48* (2013.01); *A61L 31/06* (2013.01);
(Continued)

(58) Field of Classification Search
CPC .......... A61F 2/0063; Y10T 428/1362; Y10T 428/1369; Y10T 428/249922;
(Continued)

(56) References Cited

U.S. PATENT DOCUMENTS 3,598,122 A   8/1971 Zaffaroni
3,598,123 A   8/1971 Zaffaroni
(Continued)

FOREIGN PATENT DOCUMENTS

CA   2307637   5/1999
CA   2259098   7/1999
(Continued)

OTHER PUBLICATIONS

Abate, et al., 'Separation and structural characterizations of cyclic and open chain oligomers produced in the partial pyrolysis of microbial poly(hydroxyutyrates)', Macromolecules,#s(28#23):7911-1916 (1996).
(Continued)

*Primary Examiner* — Vincent Tatesure
(74) *Attorney, Agent, or Firm* — Pabst Patent Group LLP (57) ABSTRACT

Absorbable polyester fibers, braids, and surgical meshes with prolonged strength retention have been developed. These devices are preferably derived from biocompatible copolymers or homopolymers of 4-hydroxybutyrate. These devices provide a wider range of in vivo strength retention properties than are currently available, and could offer additional benefits such as anti-adhesion properties, reduced risks of infection or other post-operative problems resulting from absorption and eventual elimination of the device, and competitive cost. The devices may also be particularly suitable for use in pediatric populations where their absorption should not hinder growth, and provide in all patient populations wound healing with long-term mechanical stability. The devices may additionally be combined with autologous, allogenic and/or xenogenic tissues to provide implants with improved mechanical, biological and handling properties.

11 Claims, 3 Drawing Sheets

Related U.S. Application Data of application No. 10/835,926, filed on Apr. 30, 2004, now Pat. No. 8,034,270.

(60) Provisional application No. 60/563,096, filed on Apr. 16, 2004, provisional application No. 60/545,771, filed on Feb. 19, 2004, provisional application No. 60/534,065, filed on Jan. 2, 2004, provisional application No. 60/469,469, filed on May 8, 2003.

(51) Int. Cl.

| | |
|---|---|
| *A61L 27/18* | (2006.01) |
| *A61L 31/06* | (2006.01) |
| *D01F 6/62* | (2006.01) |
| *D01F 6/84* | (2006.01) |
| *D01D 5/088* | (2006.01) |
| *D01D 5/16* | (2006.01) |
| *D02G 3/02* | (2006.01) |
| *D01D 5/098* | (2006.01) |
| *B29C 47/00* | (2006.01) |
| *B29C 71/00* | (2006.01) |
| *B29K 67/00* | (2006.01) |
| *B29L 31/00* | (2006.01) |

(52) U.S. Cl.
CPC ...... *B29C 47/0004* (2013.01); *B29C 47/0014* (2013.01); *B29C 71/0072* (2013.01); *D01D 5/088* (2013.01); *D01D 5/098* (2013.01); *D01D 5/16* (2013.01); *D01F 6/62* (2013.01); *D01F 6/625* (2013.01); *D01F 6/84* (2013.01); *D02G 3/02* (2013.01); *A61F 2002/0068* (2013.01); *B29K 2067/00* (2013.01); *B29L 2031/753* (2013.01); *Y10T 428/1362* (2015.01); *Y10T 428/1369* (2015.01); *Y10T 428/249922* (2015.04); *Y10T 442/10* (2015.04); *Y10T 442/183* (2015.04); *Y10T 442/184* (2015.04); *Y10T 442/2525* (2015.04)

(58) Field of Classification Search
CPC ............... Y10T 442/10; Y10T 442/183; Y10T 442/184; Y10T 442/2525
USPC ................... 606/151; 424/93.7, 443; 442/50
See application file for complete search history.

(56) References Cited

U.S. PATENT DOCUMENTS

| | | |
|---|---|---|
| 3,731,683 A | 5/1973 | Zaffaroni |
| 3,797,494 A | 3/1974 | Zaffaroni |
| 3,982,543 A | 9/1976 | Schmitt |
| 4,031,894 A | 6/1977 | Urquhart |
| RE30,170 E | 12/1979 | Goodman |
| 4,201,211 A | 5/1980 | Chandrasekaran |
| 4,205,399 A | 6/1980 | Shataby |
| 4,286,592 A | 8/1981 | Chandrasekeran |
| 4,314,557 A | 2/1982 | Chandrasekaran |
| 4,379,454 A | 4/1983 | Campbell |
| 4,435,180 A | 3/1984 | Leeper |
| 4,537,738 A | 8/1985 | Holmes |
| 4,559,222 A | 12/1985 | Enscore |
| 4,573,995 A | 3/1986 | Chen |
| 4,588,580 A | 5/1986 | Gale |
| 4,603,070 A | 7/1986 | Steel |
| 4,645,502 A | 2/1987 | Gale |
| 4,648,978 A | 3/1987 | Makinen |
| 4,664,655 A | 5/1987 | Orentreich |
| 4,704,282 A | 11/1987 | Campbell |
| 4,711,241 A | 12/1987 | Lehmann |
| 4,743,257 A | 5/1988 | Tormala |
| 4,758,234 A | 7/1988 | Orentreich |
| 4,788,062 A | 11/1988 | Gale |
| 4,792,336 A | 12/1988 | Hlavacek |
| 4,816,258 A | 3/1989 | Nedberge |
| 4,826,493 A | 5/1989 | Martini |
| 4,849,226 A | 7/1989 | Gale |
| 4,853,226 A | 8/1989 | Machida |
| 4,856,188 A | 8/1989 | Sibalis |
| 4,876,331 A | 10/1989 | Doi |
| 4,880,592 A | 11/1989 | Martini |
| 4,908,027 A | 3/1990 | Enscore |
| 4,910,145 A | 3/1990 | Holmes |
| 4,938,763 A | 7/1990 | Dunn |
| 4,943,435 A | 7/1990 | Baker |
| 5,002,067 A | 3/1991 | Berthelsen |
| 5,026,381 A | 6/1991 | Li |
| 5,032,638 A | 7/1991 | Wang |
| 5,041,100 A | 8/1991 | Rowland |
| 5,085,629 A | 2/1992 | Goldberg |
| 5,124,371 A | 6/1992 | Tokiwa |
| 5,128,144 A | 7/1992 | KorsatkoWabnegg |
| 5,171,308 A | 12/1992 | Gallagher |
| 5,204,382 A | 4/1993 | Wallace |
| 5,236,431 A | 8/1993 | Gogolewski |
| 5,245,023 A | 9/1993 | Peoples |
| 5,250,430 A | 10/1993 | Peoples |
| 5,271,961 A | 12/1993 | Mathiowitz |
| 5,278,201 A | 1/1994 | Dunn |
| 5,278,202 A | 1/1994 | Dunn |
| 5,278,256 A | 1/1994 | Bellis |
| 5,292,860 A | 3/1994 | Shiotani |
| 5,306,286 A | 4/1994 | Stack |
| 5,334,698 A | 8/1994 | Witholt |
| 5,412,067 A | 5/1995 | Shinoda |
| 5,443,458 A | 8/1995 | Eury |
| 5,468,253 A | 11/1995 | Bezwada |
| 5,480,394 A | 1/1996 | Ishikawa |
| 5,480,794 A | 1/1996 | Peoples |
| 5,489,470 A | 2/1996 | Noda |
| 5,502,116 A | 3/1996 | Noda |
| 5,502,158 A | 3/1996 | Sinclair |
| 5,512,669 A | 4/1996 | Peoples |
| 5,516,565 A | 5/1996 | Matsumoto |
| 5,516,883 A | 5/1996 | Hori |
| 5,534,432 A | 7/1996 | Peoples |
| 5,536,564 A | 7/1996 | Noda |
| 5,550,173 A | 8/1996 | Hammond |
| 5,551,954 A | 9/1996 | Buscemi |
| 5,563,239 A | 10/1996 | Hubbs |
| 5,584,885 A | 12/1996 | Becket |
| 5,614,576 A | 3/1997 | Rutherford |
| 5,625,030 A | 4/1997 | Williams |
| 5,629,077 A | 5/1997 | Turnlund |
| 5,635,215 A | 6/1997 | Boschetti |
| 5,646,217 A | 7/1997 | Hammond |
| 5,648,100 A | 7/1997 | Boschetti |
| 5,670,161 A | 9/1997 | Healy |
| 5,703,160 A | 12/1997 | Dehennua |
| 5,705,187 A | 1/1998 | Unger |
| 5,709,854 A | 1/1998 | GriffithsCima |
| 5,711,933 A | 1/1998 | Bichon |
| 5,728,752 A | 3/1998 | Scopelianos |
| 5,735,863 A | 4/1998 | DellaValle |
| 5,753,364 A | 5/1998 | Rutherford |
| 5,753,708 A | 5/1998 | Koehler |
| 5,783,271 A | 7/1998 | Nishida |
| 5,789,536 A | 8/1998 | Liggat |
| 5,811,272 A | 9/1998 | Snell |
| 5,814,071 A | 9/1998 | McDevitt |
| 5,814,599 A | 9/1998 | Mitragotri |
| 5,824,333 A | 10/1998 | Scopelianos |
| 5,824,751 A | 10/1998 | Hori |
| 5,834,582 A | 11/1998 | Sinclair |
| 5,840,331 A | 11/1998 | VanCauter |
| 5,842,477 A | 12/1998 | Naughton |
| 5,855,619 A | 1/1999 | Caplan |
| 5,874,040 A | 2/1999 | Liggat |
| 5,876,452 A | 3/1999 | Athanasiou |
| 5,876,455 A | 3/1999 | Harwin |
| 5,879,322 A | 3/1999 | Lattin |
| 5,917,002 A | 6/1999 | Doi |

(56) References Cited

U.S. PATENT DOCUMENTS

| | | | |
|---|---|---|---|
| 5,919,478 A | 7/1999 | Landrau |
| 5,935,506 A | 8/1999 | Schmitz |
| 5,990,162 A | 11/1999 | Scharf |
| 5,994,478 A | 11/1999 | Asrar |
| 6,056,970 A | 5/2000 | Greenawalt |
| 6,119,567 A | 9/2000 | Schindler |
| 6,162,531 A | 12/2000 | Martin |
| 6,214,387 B1 | 4/2001 | Berde |
| 6,245,537 B1 | 6/2001 | Williams |
| 6,316,262 B1 | 11/2001 | Huisman |
| 6,323,010 B1 | 11/2001 | Skraly |
| 6,454,811 B1 | 9/2002 | Sherwood |
| 6,514,515 B1 | 2/2003 | Williams |
| 6,548,569 B1 | 4/2003 | Williams |
| 6,555,123 B2 | 4/2003 | Williams |
| 6,600,010 B2 | 7/2003 | Mao |
| 6,610,764 B1 | 8/2003 | Martin |
| 6,623,749 B2 | 9/2003 | Williams |
| 6,645,622 B2 | 11/2003 | Yamane |
| 6,656,489 B1 | 12/2003 | Mahmood |
| 6,680,046 B1 | 1/2004 | Boschetti |
| 6,770,356 B2 | 8/2004 | ODonnell |
| 6,838,492 B2 | 1/2005 | Williams |
| 6,838,493 B2 | 1/2005 | Williams |
| 6,867,247 B2 | 3/2005 | Williams |
| 6,878,758 B2 | 4/2005 | Signer |
| 7,179,883 B2 | 2/2007 | Williams |
| 7,244,442 B2 | 7/2007 | Williams |
| 7,268,205 B2 | 9/2007 | Williams |
| 7,553,923 B2 | 6/2009 | Williams |
| 2002/0028243 A1 | 3/2002 | Masters |
| 2002/0156150 A1 | 10/2002 | Williams |
| 2002/0173558 A1 | 11/2002 | Williams |
| 2003/0091803 A1 | 5/2003 | Bond |
| 2003/0185896 A1 | 10/2003 | Buiser |
| 2003/0211131 A1 | 11/2003 | Martin |
| 2004/0220355 A1 | 11/2004 | Whitehouse |
| 2005/0107505 A1 | 5/2005 | Shinoda |
| 2005/0267516 A1 | 12/2005 | Soleimani |
| 2006/0058470 A1 | 3/2006 | Rizk |

FOREIGN PATENT DOCUMENTS

| | | |
|---|---|---|
| CA | 2298421 | 2/2000 |
| DE | 3937649 | 5/1991 |
| EP | 0258781 | 3/1988 |
| EP | 0344704 | 12/1989 |
| EP | 0349505 | 3/1990 |
| EP | 0423484 | 4/1991 |
| EP | 0429403 | 5/1991 |
| EP | 0432443 | 6/1991 |
| EP | 0452111 | 10/1991 |
| EP | 0507554 | 10/1992 |
| EP | 0601885 | 6/1994 |
| EP | 0628586 | 12/1994 |
| EP | 0754467 | 1/1997 |
| EP | 1130043 | 9/2001 |
| EP | 1266984 | 12/2002 |
| GB | 2166354 | 5/1986 |
| JP | 62209144 | 9/1987 |
| JP | 03187386 | 8/1991 |
| JP | 04292619 | 10/1992 |
| JP | 4326932 | 11/1992 |
| JP | 5023189 | 2/1993 |
| JP | 5194141 | 11/1993 |
| JP | 06264306 | 9/1994 |
| JP | 06336523 | 12/1994 |
| JP | 7275344 | 10/1995 |
| JP | 08089264 | 4/1996 |
| JP | 08218216 | 8/1996 |
| JP | 09098793 | 4/1997 |
| JP | 09507091 | 7/1997 |
| JP | 00220032 | 8/2000 |
| WO | 9218164 | 10/1992 |
| WO | 9305824 | 4/1993 |
| WO | 9320134 | 10/1993 |
| WO | 9402184 | 2/1994 |
| WO | 9406886 | 3/1994 |
| WO | 9503356 | 2/1995 |
| WO | 9517216 | 6/1995 |
| WO | 9520614 | 8/1995 |
| WO | 9520615 | 8/1995 |
| WO | 9520621 | 8/1995 |
| WO | 9523250 | 8/1995 |
| WO | 9533874 | 12/1995 |
| WO | 9600263 | 1/1996 |
| WO | 9608535 | 3/1996 |
| WO | 9618420 | 6/1996 |
| WO | 9621427 | 7/1996 |
| WO | 9640304 | 12/1996 |
| WO | 9704036 | 2/1997 |
| WO | 9707153 | 2/1997 |
| WO | 9715681 | 5/1997 |
| WO | 9730042 | 8/1997 |
| WO | 9804292 | 2/1998 |
| WO | 9839453 | 9/1998 |
| WO | 9848028 | 10/1998 |
| WO | 9851812 | 11/1998 |
| WO | 9911196 | 3/1999 |
| WO | 9914313 | 3/1999 |
| WO | 9932536 | 7/1999 |
| WO | 9935192 | 7/1999 |
| WO | 0051662 | 9/2000 |
| WO | 0056376 | 9/2000 |
| WO | 0110421 | 2/2001 |
| WO | 0115671 | 3/2001 |
| WO | 0119361 | 3/2001 |
| WO | 02085983 | 10/2002 |
| WO | 04101002 | 11/2004 |

OTHER PUBLICATIONS

Abate, et al., "Thermal Degradatuion of Microbial Poly(4-hydrixybutyrate)", Macromolecules, 27:332-336 (1994).
Addolorato, et al., 'Maintaining abstinence from alcohol with gamma-hydroxybutyric acid', The Lancet, 351:38(1998).
Agostini, et al., 'Synthesis and characterization of poly-(3-hydroxybutyrate. I. Synthesis of crystallineDL-poly-13-hydroxybutyrate from DL-0-butyrolactone' Journal of Polymer Science, Part A-1, 9: 2775-2787(1971).
Akhtar, 'Physiomechanical Properties of bacterial P(HB-FIV) Polyesters and Their Uses in drug Delivery,' The BritishLibrary Document Supply Centre, UMI, (1990).
Anderson, et al, 'Occurrence, Metabolism, metabolic Role, and Industrial Uses of bacterial Polyhydroxyalkanoates', Microbiological Reviews, 54(4):450-72 (1990).
Andriamampandry, et al., 'Cloning of a rat brain succinic semialdehyde reductase involved in the synthesis of theneuromodulator yhydroxybutyrate', Biochem. J., 334:43-50 (1998).
Bailey, 'Free radical ring-opening polymerization,' J. Polym. Preprints 25:210-11 (1984).
Bailey, et al., "Synthesis of Poly-E-caprolactone via a free radical mechanism. Free radical ring-opening polymerizationof 2-methylene-1,3-dioxepane", J. Polym. Sci. Polym. Chem., 20:3021.30 (1982).
Bandiera, et al., 'Effect of sodium sulfonate groups on the ionic conductivity of a copolyester of thiodipropionic acid',Eur. Pol. J., 33:1679-1683 (1997).
Behrend, 'PHB as a bioresorbable material for intravascular stents,' American J. Cardiol. p. 45, TCT Abstracts (Oct. 1998).
Berde, et al., 'Sustained release of dibucaine from a biodegradable polymer matrix: A potential method for protoogedneural blockade', Abstracts of Scientific Papers, 1990 Annual Meeting, Ameri. Soc. Anesthesiologists, 73(3A):A776, Sep. 1990.
Berger, et al., 'PHB recovery by hypochlorite digestion of non-PHB biomass', Biotechnonology Techniques, 3(4)227 232 (1989).
Blight, 'Miracles and molecules—progress in spinal cord repair.,' Nat. Neurosci 5:1051-4 (2002).
Boeree, et al., 'Development of a degradable composite for orthopaedic use: mechanical evaluation of anhydroxyapatite-polyhydroxybutyrate composite material', Biomaterials, 14(10):793-6 (1993).

(56) References Cited

OTHER PUBLICATIONS

Brandl, et al., 'Pseudomonas oleovorans as a source of poly(b-hydroxyalkanoates for potential applications asbiodegradable polyesters', Appl. Environ. Microbiol., 54:1977-1982 (1988).
Braunegg, et al., 'Polyhydroxyalkanoates, biopolyesters from renewable resources: physiological and engineeringaspects', J. Biotech. 65: 127-161 (1998).
Breuer, et al., 'Tissue Engineering Lamb Heart Valve Leaflets,' Biotechnology & Bioengineering 50:562-67 (1996).
Bruhn & Muller, 'Preparation and characterization of spray-dried Poly(DL-Lactide) Micro Spheres,' Proceed. Intern.Symp. Control. Rel. Bioact. Mater. 18:668-69 (1991).
Byrom, 'Miscellaneous Biomaterials,' in Biomaterials (D. Byrom, ed.) pp. 333-359 MacMillan Publishers: London, 1991.
Campbell & Bailey, 'Mechanical properties of suture materials in vitro and after in vivo implantation in horses,' Vet.Surg, 21(5):355-61 (1992).
Chu, et al., Wound Closure Biomaterials and Devices CRC Press:Boca Raton, 1996.
Clavijo-Alvarez, et al 'Comparison of biodegradable conduits within aged rat sciatic nerve defects,' Plast ReconstrSurg. 119(6):1839-51(2007).
Colombo, et al., 'Involvement of GABA(A) and GABA(B) receptors in the mediation of discriminative stimulus effects ofgamma-hydroxybutyric acid', Physiology & Behavior, 64:293-302 (1998).
Conti et al., 'Use of polylactic acid for the preparation of microparticulate drug delivery systems,' J. Microencapsulation9:153-166 (1992).
Cookson, 'It grows on trees,' Financial Times p. 6 (Aug. 12, 1992).
Cuebas, et al, 'Mitochondrial metabolism of 3-mercaptopropionic acid. Chemical synthesis of 3-mercaptopropionylcoenzyme A and some of its S-acyl derivatives', J. Biol. Chem., 260:7330-7336 (1985).
Damien & Parsons, 'Bone graft and bone graft substitutes: a review of current technology and applications,' J. Appl.Biomater. 2(3):187-208 (1991).
Dayton, et al., 'Use of an absorbable mesh to repair contaminated abdominal-wall defects'Archives of Surgery 121(8): 954-960 (1986).
De Groot, 'Meniscal tissue regeneration in porous 50150 copoly(L-lactide/epsiloncaprolactone) implants', Biomaterials, 18(8):613-622 (1997).
De Koning, et al., 'A biodegradable rubber by crosslinking poly (hydroxyalkanoate) from Pseudomonas oleovorans',Polymer, 35:2090-97 (1994).
De Smet, et al., 'Characterization of intracellular inclusions formed by Pseudomonas oleovorans duringgrowth on octane,' J. Bacteriol., 154: 870-78 (1983).
Defintion of "Region" from dictionary.com, accessed Nov. 15, 2010.
Domb, et al., Handbook of Biodegradable Polymers (Harwood Academic Publishers:Amsterdam, The Netherlands,1997).
Dubois, et al., 'Macromolecular engineering of polylactones and polylactides. 12. Study of thedepolymerization reactions of poly(e-caprolactone) with functional aluminum alkoxide end groups,'Macromolecules, 26: 4407-4412 (1993).
Duvernoy, et al., 'A biodegradable patch used as a pericardial substitute after cardiac surgery: 6- and 24-month evaluation with CT', Thorac. Cardiovasc. Surg., 43(5):271-74 (1995).
Encyclopedic Handbook of Biomaterials and Bioengineering, Part A: Materials, Val 1 eds. Wise, et al.; Marcel Dekker, Inc., NewYork, 1995.
Entholzner, et al., 'EEG changes during sedation with gamma-hydroxybutyric acid', Anaesthesist, 44:345-350(1995).
Ferreira, et al., "Films of Poly (L-Lactic Acid) /Poly(Hydroxybutyrate-co-Hydroxyvalerate) Blends:In vitro Degradation", Materials Research, 4(1):34-42 (2001).
Fraser, et al., 'Controlled release of a GnRH agonist from a polyhydroxybutyric acid implant-reversible suppression of themenstrual cycle in the macaque', Acta Endocrinol, 121:841-848 (1989).
Freed, et al., 'Biodegradable polymer scaffolds for tissue engineering', Biotechnology, 12:689-693 (1994).

Fuchtenbusch, et al., 'Biosynthesis of novel copolyesters containing 3-hydroxypivalic acid by Rhodoccus tuberNCIMB 40126 and related bacteria', FEMS Microbiol. Left., 159:85-92 (1998).
Fukuzaki, et al., 'Direct copolymerization of L-lactic acid with y-butyrolactone in the absence of catalysts,' DieMadromoleculare Chemie 190:1553-59 (1989).
Gabbay, et al., 'New outlook on pericardial substitution after open heart operations', Ann. Thorac. Surg., 48(6):803-12(1989).
Gagnon, et al., 'A thermoplastic elastomer produced by the bacterium Pseudomonas oleovarans', Rubber World, 207:32-38 (1992).
Gagnon, et al., 'Chemical modification of bacterial elastomers: 1. Peroxide crosslinking,' Polymer 35:4358-67 (1994).
Gerngross & Martin, 'Enzyme-catalyzed synthesis of poly[(R)-(+3-hydroxybutyrate]: formation of macroscopicgranules in vitro,' Proc. Natl. Acad. Sci. USA 92:6279-83 (1995).
Gerra, et al., 'Flumazenil effects on growth hormone response to gammahydroxybutyric acid', International ClinicalPsychopharmacology, 9:211-215 (1994).
Gordeyev, et al., "Processing of gel-spun poly($^2$-hydroxybutyrate) fibers", Journal of Applied Polymer Science, 81:2260-2264 (2001).
Griebel, et al., 'Metabolism of poly-beta-hyclroxybutyrate I. Purification, composition, and properties of native poly-beta-hydroxybutyrate granules from Bacillus megaterium', Biochemistry, 7:3676-3681 (1968).
Gross, et al., 'Polymerization off/-monosubstituted-O-propiolactones using trialkylaluminum-watercatalytic systems and polymer characterization,' Macromolecules, 21: 2657-2668 (1988).
Gugala, et al., Regeneration of segmental diaphyseal defects in sheep tibiae using resorbable polymeric membranes: apreliminary study, J. Otthop. Trauma. 13(3):187-95 (1999).
Gursel,.et al., 'In vivo application of biodegradable controlled antibiotic release systems for the treatmentof implant-related osteomyelitis,' Biomaterials 22: 73-80 (2001).
Hadlock, et al., 'Ocular cell monolayers cultured on biodegradable substrates,' Tissue Eng. 5(3):187-96 (1999).
Hazari, et a/., 'A new resorbable wrap-around implant as an alternative nerve repair technique', J. Hand Surgery, 24(3):291-295 (1999).
Hazari et al., 'A resorbable nerve conduit as an alternative to nerve autograft in nerve gap repair', Br J Plast Surg.,52(8):653-7 (1999).
Hein, et al., 'Biosynthesis of poly(4-hydroxybutyric acid) by recombinant strains of *Escherichia coli*', FEMS Microbiol.Lett. 153:411-18 (1997).
Heydorn, et al., 'A new look at pericardial substitutes,' J. Thorac. Cardiovasc. Surg, 94:291-96 (1987).
Hocking and Marchessault, 'Syndiotactic poly[(R,S)-0-hydroxybutyrate] isolated frommethylaluminoxane-catalyzed polymerization,' Polym. Bull., 30: 163-170 (1993).
Hocking and Marchessault, Chemistry and Technology of Biodegradable Polymers, inBiopolyesters (G.J.L. Griffin, Ed.), Chapman and Hall, London, pp. 48-96 (1988).
Hoke, 'Mechanisms of Disease: what factors limit the success of peripheral nerve regeneration in humans?' Nat. Clin.Pract. NeuroL 448-454 (2006).
Holmes, Biologically Produced (R)-3-hydroxyalkanoate Polymers and Copolymers, in Developments in Crystalline Polymers (D.C. Bassett Ed.), Elsevier, London, vol. 2, pp. 1-65 (1988).
Holmes, et al., 'Applications of PHBa microbially produced biodegradable thermoplastic,' Phys Technol 16:32-36(1985).
Hori, et al., 'Chemical synthesis of high molecular weight poly(3-hydroxybutyrate-co-4-hydroxybutyrate)' Polymer 36(24): 4703-4705 (1995).
Hori, et al., 'Ring-opening copolymerization of optically active 0-butyrolactone with several lactonescatalyzed by distannoxane complexes: synthesis of new biodegradable polyesters,' Macromolecules, 26:4388-4390 (1993).
Hori, et al., "Ring-Opening Polymerization of Optically Active 11-Butyrolactone Using Distannoxane Catalysts: Synthesisof High Molecular Wright Poly(3-hydroxybutyrate)," Macromolecules 26:5533-34 (1993).
Horowitz, et al., 'Novel Thermal Route to an Amorphous, Film-Forming Polymer Latex', Macromolecules, 32:3347 3352 (1999).

(56) References Cited

OTHER PUBLICATIONS

Horsch, 'Inheritance of Functional Foreign Genes in Plants', Science, 223 (4635):496-498 (1984).
Huijberts, et al., 'Pseudomonas putida KT2442 cultivated on glucose accumulates poly(3-hydroxyalkanoates)consisting of saturated and unsaturated monomers', Appl Environ Microbiot, 58(2):536-44 (1992).
Hutmacher, et al., 'A review of material properties of biodedradable and bioresorbable polymers and devices for GTRand GBR applications,' Int. J. Oral Maxillofac. Implants 11(5):667-78 (1996).
Kameyama, et al., 'Novel sequence ordered polymers by transformation of polymer backbone: Quantitative andregioselective insertion of Thiranes into poly( S-aryl thioester)', Macrornot, 32:1407-1412 (1999).
Kassab, 'Rifampicin carrying polyhydroxybutyrate microspheres as a potential chemoembolization agent', Journal of Biomaterials Science, Polymer Edition, 8(12):947-961 (1997).
Kassab, et al., 'Embolization with polyhydroxybutyrate (PHB) microspheres: In vivo studies', J. Bioact. Compat. Polym.,14:291-303 (1999).
Kaufman and Nelson, 'An overview of gamma-hydroxybutyrate catabolism: the role of the cytosolic NADP(+) dependent oxidoreductase EC 1.1.1.19 and of a mitochondrial hydroxyacid-oxoacid transhydrogenase in the initial, rate limiting step in this pathway', Neurochemical Research, 16:965-974 (1991).
Keeler, 'Don't Let Food Go to Waste—Make Plastic Out of It,' R&D Magazine pp. 52-57 (1991).
Keeler, 'Plastics Grown in Bacteria Inch Toward the Market,' R&D Magazine pp. 46-52 (1991).
Kemnitzer, et al., 'Preparation of predominantly syndiotactic poly(/3-hydroxybutyrate) by the tributyltinmethoxide catalyzed ring-opening polymerization of racemic /3-butyrolactone,' Macromolecules, 26:1221-1229 (1993).
Kim and Mooney, 'Engineering smooth muscle tissue with a predefined structure', J. Biomed. Mat. Res., 41(2):322-332(1998).
Kishida, et al. 'Formulation assisted biodegradeable polymer matrices' Chemical and Pharmaceutical Bulletin, JP Pharm Society of Japan. 37(7):1954-1956(1989).
Kleinschmidt, et al., 'Continuous sedation during spinal anaesthesia: gamma-hydroxybutyrate vs. propofol', European Journalof Anaesthesiology, 16:23-30 (1999).
Kleinschmidt, et al., 'Total intravenous anaesthesia using propofol, gamma-hydroxybutyrate or midazolam in combination withsufentanil for patients undergoing coronary artery bypass surgery', European Journal of Anesthesiology, 14:590-599 (1997).
Klinge, et al., 'Functional assessment and tissue response of short- and long-term absorbablesurgical meshes' Biomaterials 22: 1415-1424 (2001).
Koosha, 'Preparation and characterization of biodegradable polymeric drug carriers,' Ph.D. Dissertation, 1989, Univ.Nottingham, UK., Diss. Abstr. Mt. B 51:1206 (1990).
Koosha, et al., 'Polyhydroxybutyrate as a drug carrier,' Crit. Rev. Ther. Drug Carrier Syst. 6(2):117-30 (1989).
Korkusuz, et al., In vivo response to biodegradable controlled antibiotic release systems, J. Biomed. Mater. Res. 55:217-228 (2001).
Korsatko, et al., 'The influence of the molecular weight of poly-D(-)-3-hydroxybutyric acid on its use as a retard matrixfor sustained drug release,' 8th Europ. Congress of Biophannaceutics and Pharmokinetics 1:234-242 (1987).
Korte & Gelt, 'Hochdruckreaktionen. II. Die Polymerisation Von y butyrolacton and 6-valerolactam bei hohendriicken,' Polymer Lett. 4:685-89 (1966).
Kusaka, et al., 'Microbial synthesis and Physical Properties of ultra-high-molecular-weight poly((R)-3-hydroxybutyrate]', PureAppl. Chem., A35:319-35 (1998).
Lafferty, et al., 'Microbial Production of Poly-b-hydroxvbutvric acid' in Biotechnolooy (H.J. Rehm and G. Reed, eds.), Verlagsgesellschaft, Weinheim, vol. 66, pp. 135-176 (1988).

Lamba, et al., Degradation of polyurethane?, in Polyurethanes in Biomedical Applications (CRC Press:Boca Raton, Florida, 1998).
Lanza, et al., Principles of Tissue Engineering (Academic Press:Austin, 1997).
Le Borgne and Spassky, 'Stereoelective polymerization of (3-butyrolactone,' Polymer, 30: 2312-2319(1989).
Lebedev and Yevstropov, 'Thermoplastic properties of palylactones', Makromol. Chem., 185:1235-1253 (1984).
Lee, et al., 'Copolymerization of y-butyrolactone and II-butyrolactone', Macromol. Chem. Phys., 198:1109-1120 (1997).
Lemoigne & Roukhelman, 'Fermetation 6-Hydroxybutyrique Caracterisation et Evolution Des Produits deDeshydration et de Polymerisation de L'acide 11-Dehydroxybutyrique,' Annales des fermentations, 5:527-36 (1925).
Ljungberg, et al. 'Neuronal survival using a resorhable synthetic conduit as an alternative to primary nerve repair',Microsurgery, 19(6):259-264 (1999).
Lloyd, et al. 'Transformation of *Arabidopsis thalania* with Agrobacterium tumefaciens,' Science 234: 464-66 (1986).
Lutke-Eversloh et al., 'Identification of a new class of biopolymer: Bacterial synthesis of a sulfur-containing polymer withthioester linkages', Microbiology, 147(1): 11-19 (2001).
Lutke-Eversloh et al., 'List of submitted abstracts', The 8th International Symposium on Biological Polyesters,(2000).
Madison & Huisman, 'Metabolic engineering of poly(3-hydroxyalkanoates): from DNA to plastic,' Microbiol. Molec.Biol. Rev. 63:21-53 (1999).
Malm, et al., 'A new biodegradable patch for closure of atrial septal defect. An experimental study,' Scand. J. Thorac.Cardiovasc. Surg. 26(1):9-14 (1992).
Malm et al., 'Enlargement of the right ventricular outflow tract and the pulmonary artery with a new biodegradable patchin transannular position,' Eur. Surg. Res. 26(5):298-308 (1994).
Malm, et al., 'Prevention of postoperative pericardial adhesions by closure of the pericardium with absorbable polymerpatches. An experiments study,' J. Thorac. Cardiovasc. Surg. 104(3):600-07 (1992).
Martin and Williams, 'Medical application of poly-4-hydroxybutyrate: A strong flexible absorbablebiomaterial', Biochem. Eng. J., 16:97-105 (2003).
Math Iowitz & Langer, 'Polyanhydride microspheres as drug delivery systems' in Microcapsules Nanopart. Med. Pharm. (Donbrow, ed.), pp. 99-123 (CRC:Boca Raton, Florida, 1992).
Maysinger, et al., 'Microencapsulation and the Grafting of Genetically Transformed Cells as Therapeutic Strategies torescue Degenerating Neurons of the CNS,'Reviews in the Neurosciences, 6:15-33 (1995).
McMillin, et al., 'Elastomers for Biomedical Applications,' Rubber Chemistry and Technology 67:417-446 (1994).
McWilliams, 'Plastics as High as an Elephant's Eye?' Business Week, pp. 110-111 (1991).
Modelli, et al., 'Kinetics of aerobic polymer degradation in soil by means of the ASTM D 5988-96 standard method,' JEnviron Polym Degr 7:109-116 (1999).
Muh, et al., 'PHA synthase from chromatium vinosum: cysteine 149 is involved in covalent catalysis', Bioche., 38:826 837 (1999).
Muller, et al., 'Poly(hydroxyalkanoates): A Fifth Class of Physiologically Important Organic Biopolymers,' Angew. Chem. int. Ed. Engl. 32:477-502 (1993).
Nakamura, et al., 'Microbial synthesis and characterization of poly(3-hydroxybutyrate-co-4-hydroxybutyrate),'Macromol. 25:4237-41 (1992).
Nakamura et al., 'Biosynthesis and characteristics of bacterial poly(3-hydroxybutyrate-co-3-hydroxypropionate)',Macromol. Rep., A28, 15-24 (1991).
Nelson, et al., 'The extraneural distribution of gamma-hydroxybutyrate', J. Neurochem., 37:1345-1348 (1981).
Niklason, et al., 'Functional arteries grown in vitro,' Science 284(5413):489-93 (1999).
Nobes, et al., 'Polyhydroxyalkanoates: Materials for delivery systems,' Drug Del. 5:167-77 (1998).

(56) References Cited

OTHER PUBLICATIONS

Ogawa, et al., 'A New Technique to Efficiently Entrap Leuprolide Acetate into Microcapsules of Poly Lactic Acid orCopoly(Lactic/Glycolic) Acid,' Chem. Pharm. Bull. 36:1095-103 (1988).
Otera, et al., 'Distannoxane-catalysed transesterification of 1,n-Dioldiacetates, Selective transformation of either ofchemically equivalent functional groups,' J. Chem. Soc. Chem. Commun. 1742-43 (1991).
Otera, et al., 'Distannoxane as reverse micelle-type catalyst: novel solvent effect on reaction rate of transesterification,'J. Org. Chem. 54:4013-14 (1989).
Otera, et al., 'Novel distannoxane-catalyzed transesterification and a new entry to 0,3-unsaturated carboxylic acids,'Tetrahedron Lett., 27:2383-86 (1986).
Otera, et al., 'Novel template effects of distannoxanne catalysts in highly efficient transesterification and esterification,'J. Org. Chem, 56:5307-11 (1991).
Pedros Alio et al., 'The influence of poly-3-hydroxybutyrate accumulation on cell volume and buoyant density inAlcaligenes eutrophus', Arch. Microbiol. 143:178-184 (1985).
Peoples, et al., 'Poly-3-hydroxybutyrate Biosynthesis in Alcaligenes eutrophus H16,' J. Biol. Chem 264(26):15293-97(1989).
Peoples, et al., 'Polyhydroxybutyrate (PHB): A Model System for Biopolymer Engineering: II,' in Novel Biodegradable Microbial Polymers (Dawes, ed.) pp. 191-202, Kluwer Academic Publishers:Netherlands (1990).
Perrin & English, 'Polycaprolactone,' in Handbook of Bioabsorbable Polymers (Domb, et al., eds.) pp. 63-77 (Harwood, Amsterdam, 1997).
Pinto, 'Hydrogen Peroxide as depyrogenation agent for medical devices components', Revista De Saude Publica,29(1):75-79 (1995).
Poirier, 'Perspectives on the production of polyhydroxyalkanoates in plants,' FEMS Microbiology Reviews 103:237-46(1992).
Poirier, et al., 'Progress Toward Biologically Produced Biodegradable thermoplastics,' Adv. Mater. 5(1):30-37 (1993).
Pool, 'In Search of the Plastic Potato,' Science 245: 1187-89 (1989).
Pouton & Akhtar, 'Biosynthetic polyhydroxyalkanoates and their potential in drug delivery,' Adv. Drug Delivery Rev. 18:133-62 (1996).
Rehm and Steinbuchel, 'Biochemical and genetic analysis of PHA synthases and other proteins required for PHAsynthesis', Int. J. Biol. Macromol. 25:3-19 (1999).
Renstad, et al., 'The influence of processing induced differences in molecular structure on the biological and non biological degradation of poly (2-hydroxybutyrate-co-3-hydroxyvalerate), P(3-HB-co-3-HV),' Polymer Degradation andStability 83:201-211 (1999).
Reynolds, Martindale: The Extra Pharmacopeia, p. 1264, (Thirty First Edition, Royal Pharmaceutical Society, London, 1997).
Rivard, et al., 'Fibroblast seeding and culture in biodegradable porous substrates,' J. Apt Biomater. 6(1):65-68(1995).
Ropero-Miller & Goldberger, 'Recreational drugs. Current trends in the 90s', Clinics in Laboratory Medicine, 18:727-746 (1998).
Sabbagh, et al., '3-Mercaptopropionic acid, a potent inhibitor of fatty acid oxidation in rat heart mitochondria', J. Biol.Chem. 260:7337-7342 (1985).
Saito, et al., 'Microbial synthesis and properties of poly(3-hydroxybutyrate-co-4-hydroxybutyrate) in Comamonasacidovorans,' Int. J. Biol. Macromol. 16(2):99-104 (1994).
Scharf, et al, 'Pharmacokinetics of gammahydroxybutyrate (GHB) in narcoleptic patients', Sleep 21:507-514 (1998).
Schlegel, et al., 'Ein submersverfahren zur kultur wasserstoffoxydierender bakterien: Wachstumsphysiologlscheuntersuchungen', Arch. Mikrobiol, 38:209-222 (1961).
Schlosshauer, 'Synthetic nerve guide implants in humans: a comprehensive survey.' Neurosurgery 59:740-748(2006).
Schmidt, et al 'Neural tissue engineering: strategies for repair and regeneration,' Annu. Rev. Biomed. Eng. 5:293-347(2003).
Schwartz & Goodman, Plastic Materials and Processes (Van Nostrand Reinhold Company:New York, 1982).
Sendelbeck & Girdis, 'Disposition of a 14C-labeled bioerodible polyorthoester and its hydrolysis products, 4-hydroxybutyrate and cis,trans-1,4-bis(hydroxymethyl)cyclohexane, in rats', Drug Metabolism & Disposition 13:291-295(1985).
Shinoka, et al., 'Creation of viable pulmonary artery autografts through tissue engineering,' J. Thorac. Cardiovasc.Surg. 115(3):536-46 (1998).
Shinoka, et al., 'Tissue engineering heart valves: valve leaflet replacement study in a lamb model' Ann. Thorac. Surg.60(6 Suppl):S513-16 (1995).
Shinoka & Mayer, 'New frontiers in tissue engineering: tissue engineered heart valves' in Synthetic Bioabsorbable Polymer Scaffolds (Atala & Mooney, eds.) pp. 187-198 Birkhalser Boston, 1997.
Sim, et al., 'PHA synthase activity controls the molecular weight and polydispersity of polyhydroxybutyrate in vivo,' Nat.Biotechnol, 15(1):63-67 (1997).
Skrede et al, 'Thia fatty acids, metabolism and metabolic effects' In Biochim Biophys Acta 1344:115-31 (1997).
Snead, 'The gamma-hydroxybutyrate model of absence seizures: correlation of regional brain levels of gamma hydroxybutyric acid and gamma-butyrolactone with spike wave discharges', Neuropharmacology 30:161-167 (1991).
Song, et al., 'Production of poly(4-hydroxybutyric acid) by fed-batch cultures of recombinant strains of Escherichia coli',BiotechnoL Lett. 21:193-197 (1999).
Speer & Warren, 'Arthroscopic shoulder stabilization. A role for biodegradable materials,' Clin. Otthop. (291):67-74(1993).
Stanton & Gagne, 'The remarkable catalytic activity of alkali-metal alkoxide clusters in the ester interchangereaction,' J. Am. Chem. Soc. 119:5075-76 (1997).
Steinbuchel, 'Molecular basis for biosynthesis and accumulation of polyhydroxyalkanoic acids in bacteria,' FEMSMicrobial. Rev. 103:217-230 (1992).
Steinbuchel, 'Polyhydroxyalkanoic acids' in Biomaterials: Novel Materials from Biological Sources (Byrom; D.,ed.),pp. 123-213, Grove's-Dictionaries: Stockton, New-York (1991).
Steinbuchel, et al. 'Diversity of Bacterial Polyhydroxyalkanoic Acids', FEMS Microbial. Lett. 128:219-228 (1995).
Steinbuchel & Wiese, 'A Pseudomonas strain accumulating polyesters of 3-hydroxybutyric acid and medium-chain length 3-hydroxyalkanoic acids,' Appl. Microbiol. Biotechnol. 37:691-97 (1992).
Takagi et al., 'Biosynthesis of polyhydroxyalkanoate with a thiophenoxy side group obtained from Pseudomonasputida', Macromolecules, 32: 8315-8318 (1999).
Talja, et al., 'Bioabsorbable and biodegradable stents in urology,' J. Endourol. 11(6):391-97 (1997).
Tanahashi, et al., 'Thermal Properties and Stereoregularity of Poly(3-hydroxybutyrate) Prepared from optically Activefl-Butyrolactone with a Zinc-Based Catalyst,' Macromolecules 24:5732-33 (1991).
Tanaka, et al., 'Clinical application of 4-hydroxybutyrate sodium and 4-butyrolactone in neuropsychiatric patients', PallePsychiatrica et Neurologica 20:9-17 (1966).
Tanguay, et al., 'Current status of biodegradable stents,' Cardiol. Clin. 12(4):699-713 (1994).
Tepha announces submission of device master file to FDA (Jun. 3, 2002), Retrieved Dec. 17, 2004, from http://www.pressrelease.be/script UK/newsdetail.asp?ndavs=m&ID=695.
Tepha submits device master file to FDA—New Technology (Jul. 2, 2002). Retrieved on Dec. 17, 2004, from http://www.findarticles.eom/p/articles/mi mOPC/is 7 26/ai 89018276.
Tsuruta, et al., Biomedical Applications of Polymeric Materials (CRC Press, Boca Raton, Florida, 1993).
Tunnicliff, 'Sites of action of gamma-hydroxybutyrate (GHB)—a neuroactive drug with abuse potential', ClinicalToxicology, 35:581-590 (1997).
Turesin, et al., 'Biodegradable polyhydroxyalkanoate implants for osteomyelitis therapy: in vitro antibiotic release,' J. Biomaler. Sci. Polymer Edn. 12:195-207 (2001).
Turke, 'Absorbable Biomaterial is suited for diverse applications' (Jun. 3, 2002). Retrieved on Dec. 17, 2004, from http://www.devicelink.eom/mpmn/archive/01/10/009.html.

(56) References Cited

OTHER PUBLICATIONS

Unverdorben, et al., 'Polyhydroxybutyrate (PHB) Biodegradable Sient-Experience in the Rabbit,' American J. Cardiol, p. 46, TCT Abstracts (Oct. 1998).
Valappil, et al., 'Biomedical applications of polyhydroxyalkanoates, an overview of animal testing and in vivo responses', Expert Rev. Med. Devices, 3(6):853-868 (2006).
Valentin, et al., 'Identification of 4-hydroxyhexanoic acid as a constituent of biosynthetic polyhydroxyalkanoic acidsfrom bacteria,' Appl. Microbiol. Biotechnol. 36:507-514 (1994).
Valentin, et al., 'Identification of 5-hydroxyhexanoic acid, 4-hydroxyaheptanoic acid and 4-hydroxyoctanoic acid as new constituents of bacterial polyhydroxyalkanoic acids', Appl. Microbiol. Biotechnol., 46:261-67 (1996).
Valentin, et al., 'Production of poly(3-hydroxybutyrate-co-4-hydroxybutyrate) in recombinant *Escherichia coli* grown on glucose,' J. Biotechnol. 58:33-38 (1997).
Von Schroeder, et al., 'The use of polylactic acid matrix and periosteal grafts for the reconstruction of rabbit knee articular defects', J. Biomed. Mater. Res., 25(3):329-39 (1991).
Wallen & Rohwedder, "Poly-11-hydroxyalakaonate from Activated Sludge," Environ. Sal. Technol. 8:576-79 (1974).
Widmer & Mikos, 'Fabrication of biodearadable polvmer scaffolds for tissue enaineersna' in Frontiers in Tissue Engineerinq (Patrick, etal., Eds.) Ch, II.5, pp. 107-120 (Elsevier Science, New York, 1998).
Williams, et al., 'PHA applications: addressing the price performance issue. I. Tissue engineering,' Int. J. Biol.Macromol. 25(1-3): 111-121 (1999).
Williams & Peoples, 'Biodegradable plastics from plants,' Chemtech 26:38-44 (1996).
Williams & Peoples, 'Making plastics green,' Chem. Br. 33#3A)2D#32 (1997).
Wodzinska, et al., 'Polyhydroxybutyrate synthase: Evidence covalent catalysis', J. Am. Chem. Soc. 118:6319-6320(1996).
Wong & Mooney, 'Synthesis and properties of biodegradable polymers used as synthetic matrices tor tissue engineering', in Synthetic Biodegradable Polymer Scaffolds (Atala, et al., eds.) DP. 51-82 (Birkhauser. Boston, 1997).
Worsey and Williams, 'Metabolism of toluene and xylenes by Pseudomonas putida (arvilla) mt-2: evidence for a new function of the TOL plasmid' J Bacterid 124:7-13 (1975).
Xie, et al., 'Ring-opening Polymerization of a-Butyrolactone by Thermophilic Lipases,' Macromolecules 30:6997-98(1997).
Yagmurlu, et al., 'Sulbactam-cefoparazone polyhydroxybutyrate-co-hydroxyvalerate (PHBV) local antibiotic delivery system: in vivo effectiveness and biocompatibility in the treatment of implant-related experimental osteomyelitis', J Biomed Mater Res., 46(4):494-509 (1999).
Yamada, et al., 'Development of a dural substitute from synthetic bioabsorbable polymers', J. Neurosurg., 86(6):1012-17(1997).
Yiu, et al. 'Glial inhibition of CNS axon regeneration,' Nat. Rev. Neurosci. 7:617-627 (2006).
Zund, et al., 'The in vitro construction of a tissue engineered bioprosthetic heart valve,' Eur. J. Cardiothorac. Surg.11(3):493-97 (1997).
Gursel, et al., "In vitro antibiotic release from poly(3-hydoxybutyrate-co-3-hydroxyvalerate) rods" , Microencapsulation, 19(2):153-64 (2002).

POLYHYDROXYALKANOATE MEDICAL TEXTILES AND FIBERS

CROSS REFERENCE TO RELATED APPLICATIONS

This application is a divisional of pending prior application U.S. Ser. No. 13/228,056, filed Sep. 8, 2011, which is a divisional of U.S. Ser. No. 10/835,926, filed Apr. 30, 2004, now U.S. Pat. No. 8,034,270, issued Oct. 11, 2011, entitled "Polyhydroxyalkanoate Medical Textiles and Fibers", by David P. Martin, Said Rizk, Ajay Ahuja and Simon F. Williams, which claims priority to U.S. Ser. No. 60/563,096 filed Apr. 16, 2004; U.S. Ser. No. 60/545,771 filed Feb. 19, 2004; U.S. Ser. No. 60/534,065 filed Jan. 2, 2004; and U.S. Ser. No. 60/469,469 filed May 8, 2003.

STATEMENT REGARDING FEDERALLY SPONSORED RESEARCH OR DEVELOPMENT

This invention was made with government support under grant numbers 70NANB2H3053 awarded by the U.S. Department of Commerce and 1R43GM64863-01 awarded by the National Institutes of Health Small Business Innovation Research. The government has certain rights in the invention.

BACKGROUND OF THE INVENTION

The present invention generally relates to textile and fiber-based medical devices derived from poly-4-hydroxybutyrate and its copolymers.

Figure 1:
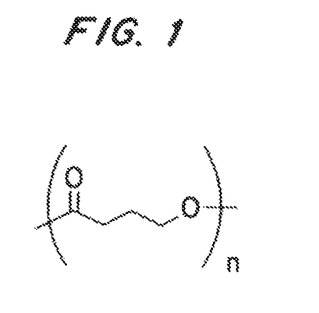
FIG. 1 is the chemical structure of poly-4-hydroxybutyrate (P4HB, poly-4-hydroxybutyrate).
Figure 2:
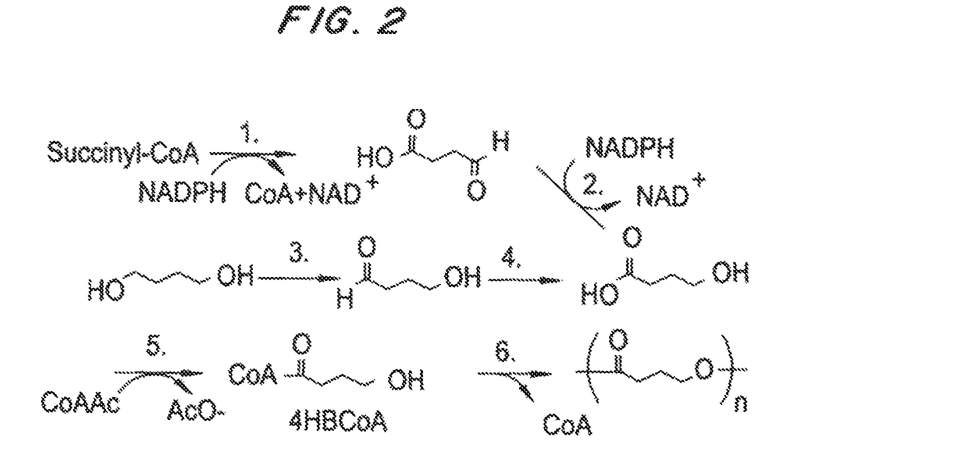
FIG. 2 shows some of the known biosynthetic pathways for the production of P4HB. Pathway enzymes are: 1. Succinic semialdehyde dehydrogenase, 2. 4-hydroxybutyrate dehydrogenase, 3. diol oxidoreductase, 4. aldehyde dehydrogenase, 5. Coenzyme A transferase and 6. PHA synthetase.

Poly-4-hydroxybutyrate (available from Tepha, Inc., Cambridge, Mass. as PHA4400) is a strong pliable thermoplastic that is produced by a fermentation process (see U.S. Pat. No. 6,548,569 to Williams et al.). Despite its biosynthetic route, the structure of the polyester is relatively simple (FIG. 1). The polymer belongs to a larger class of materials called polyhydroxyalkanoates (PHAs) that are produced by numerous microorganisms, Steinbüchel, A. Polyhydroxyalkanoic acids, *Biomaterials,* 123-213 (1991); Steinbüchel A., et al. Diversity of Bacterial Polyhydroxyalkanoic Acids, *FEMS Microbial. Lett.* 128:219-228 (1995); and Doi, Y. *Microbial Polyesters* (1990). In nature these polyesters are produced as storage granules inside cells, and serve to regulate energy metabolism. They are also of commercial interest because of their thermoplastic properties, and relative ease of production. Several biosynthetic routes are currently known to produce poly-4-hydroxybutyrate, as shown in FIG. 2. Chemical synthesis of poly-4-hydroxybutyrate has been attempted, but it has been impossible to produce the polymer with a sufficiently high molecular weight necessary for most applications, Hori, Y., et al. Chemical Synthesis of High Molecular Weight poly(3-hydroxybutyrate-co-4-hydroxybutyrate, *Polymer* 36:4703-4705 (1995).

Tepha, Inc. (Cambridge, Mass.) produces PHA4400 and related copolymers for medical use, and has filed a Device Master Files with the United States Food and Drug Administration (FDA) for PHA4400. Related copolymers include 4-hydroxybutyrate copolymerized with 3-hydroxybutyrate or glycolic acid (U.S. Ser. No. 60/379,583 to Martin & Skraly, U.S. Pat. No. 6,316,262 to Huisman et al., and U.S. Pat. No. 6,323,010 to Skraly et al.). Tepha has also filed a Device Master File with the United States FDA for copolymers containing 3-hydroxybutyrate and 4-hydroxybutyrate. Methods to control molecular weight of PHA polymers have been disclosed by U.S. Pat. No. 5,811,272 to Snell et al., and methods to purify PHA polymers for medical use have been disclosed by U.S. Pat. No. 6,245,537 to Williams et al. PHAs with degradation rates in vivo of less than one year have been disclosed by U.S. Pat. No. 6,548,569 to Williams et al. and PCT WO 99/32536 to Martin et al. The use of PHA as tissue engineering scaffolds has also been disclosed by U.S. Pat. No. 6,514,515 to Williams, and other applications of PHAs have been reviewed in Williams, S. F., et al. Applications of PHAs in Medicine and Pharmacy, in Biopolymers, *Polyesters, III* Vol. 4:91-127 (2002).

In the practice of surgery there currently exists a need for absorbable fibers and surgical meshes with improved performance. For example, there is currently a need for an absorbable monofilament fiber with a prolonged strength retention that can be used as a suture material. Such a product would potentially be useful in the treatment of patients with diabetes, obesity, nutritional impairment, compromised immune systems, or other conditions such as malignancy or infection that compromise wound healing.

There also exists a need for improved surgical meshes. For example, an absorbable hernia mesh with prolonged strength retention could have many advantages over the non-absorbable synthetic meshes currently used in hernia operations (Klinge U., et al., Functional Assessment and Tissue Response of Short- and Long-term Absorbable Surgical Meshes, *Biomaterials* 22:1415-1424 (2001). Long-term implantation of these non-absorbable meshes is not considered ideal because they can lead to complications such as adhesions (fistula formation), pain, and restriction of physical capabilities (Klinge et al., 2001). If implanted into surgical sites that are contaminated or have the potential to become contaminated, 50-90% of these non-absorbable implants will need to be removed (Dayton et al. 1986). These implants are also not ideal for use in pediatric patients where they could hinder growth (Klinge et al., 2001). To date, the use of absorbable synthetic surgical meshes in hernia repair has been found to almost invariably result in large incisional hernias that require revision operations because of the relatively short-term strength retention of these materials (Klinge et al., 2001). However, it is thought that an absorbable hernia mesh with prolonged strength retention could solve this problem providing a mechanically stable closure, reduce the incidence of adhesions and risks of infection, and be suitable for use in pediatric patients.

In addition to the need for improved meshes for hernia repair, there are also needs for improved meshes and patches for other procedures. In pericardial repair there exists a need for a surgical material that will prevent adhesions between the sternum and heart following open-heart surgery. There are also similar needs to prevent adhesions in spinal and gynecology procedures that could be addressed with improved surgical meshes and patches.

Biomaterial patches derived from animal and human tissue are currently used fairly extensively in cosmetic surgery, cardiovascular surgery, general surgery (including hernia repair), and in urology and gynecology procedures for the treatment of conditions that include vaginal prolapse and urinary incontinence. There is however reported to be growing concern about the use of animal and human derived biomaterials because of the risks associated with disease transmission. Synthetic absorbable meshes and patches that may offer decreased risks of disease transmission are currently limited, can be inflammatory, and do not provide prolonged strength retention. Thus there currently exists a need to develop new absorbable meshes for these procedures as well. Ideally, these products should have prolonged strength retention, induce minimal inflammatory responses that resolve, provide mechanically stable reinforcement or closure, offer anti-adhesion properties (where necessary), minimize the risks of disease transmission, and after absorption leave as healthy natural tissue structure.

There is thus a need to develop absorbable fibers with prolonged strength retention that could be used as suturing materials, or in surgical meshes. The latter, offering longer-term mechanical stability, could also be used in other procedures such as pelvic floor reconstruction, urethral suspension (to prevent stress incontinence using the mesh as a sling), pericardial repair, cardiovascular patching, cardiac support (as a sock that fits over the heart to provide reinforcement), organ salvage, elevation of the small bowel during radiation of the colon in colorectal cancer patients, retentive devices for bone graft or cartilage, guided tissue regeneration, vascular grafting, dural substitution, nerve guide repair, as well as in procedures needing anti-adhesion membranes and tissue engineering scaffolds. Strong absorbable fibers could also find other uses, for example, in synthetic ligament and tendon devices or scaffolds. Further uses include combinations with other synthetic and natural fibers, meshes and patches. For example, the absorbable fibers and devices such as meshes and tubes derived front the fibers could be combined with autologous tissue, allogenic tissue, and/or xenogenic tissues to provide reinforcement, strengthening and/or stiffening of the tissue. Such combinations could facilitate implantation of the autologous, allogenic and/or xenogenic tissues, as well as provide improved mechanical and biological properties. Combination devices could be used for example in hernia repair, mastopexy/breast reconstruction, rotator cuff repair, vascular grafting/fistulae, tissue flaps, pericardial patching, tissue heart valve implants, bowel interposition, and dura patching.

It is therefore an object of this invention to provide absorbable fibers, surgical meshes, and medical devices with one or more of the following features: prolonged strength retention in vivo, anti-adhesion properties, minimal inflammatory reaction upon implantation, minimal risk the disease transmission or to potentiate infection, remodeling in vivo to a healthy natural tissue.

It is another object of this invention to provide methods for fabricating the articles and devices with prolonged strength retention.

It is yet another object of the invention to provide absorbable multifilament fibers, and methods for fabricating these multifilaments into surgical meshes.

It is still yet another object of the invention to combine the fibers and meshes with autologous, allogenic and/or xenogenic tissues to provide improved mechanical, biological and handling properties of the autologous, allogenic and/or xenogenic tissues.

SUMMARY OF THE INVENTION

Absorbable polyester fibers, braids, and surgical meshes with prolonged strength retention have been developed. These devices are preferably derived from biocompatible copolymers or homopolymers of 4-hydroxybutyrate. These devices provide a wider range of in vivo strength retention properties than are currently available, and offer additional benefits such as anti-adhesion properties, reduced risks of infection or other post-operative problems resulting from absorption and eventual elimination of the device, and competitive cost. The devices are also particularly suitable for use in pediatric populations where their absorption should not hinder growth, and provide in all patient populations wound healing with long-term mechanical stability. The devices may additionally be combined with autologous, allogenic and/or xenogenic tissues to provide implants with unproved mechanical, biological and handling properties.

DETAILED DESCRIPTION OF THE INVENTION

Absorbable fibers and meshes with prolonged strength retention have been developed.

I. Definition

Strength retention refers to the amount of time that a material maintains a particular mechanical property following implantation into a human or animal. For example, if the tensile strength of an absorbable fiber decreased by half over 3 months when implanted into an animal, the fiber's strength retention at 3 months would be 50%.

Biocompatible refers to the biological response to the material or device being appropriate for the device's intended application in vivo. Any metabolites of these materials should also be biocompatible.

Poly-4-hydroxybutyrate means a homopolymer comprising 4-hydroxybutyrate units. It may be referred to as P4HB, PHA4400 or TephaFLEX™ biomaterial and is manufactured by Tepha Inc., Cambridge, Mass. Copolymers of poly-4-hydroxybutyrate mean any polymer comprising 4-hydroxybutyrate with one or more different hydroxy acid units.

II. Source of Poly-4-hydroxybutyrate and Copolymers Thereof

Tepha, Inc. of Cambridge, Mass. produces poly-4-hydroxybutyrate and copolymers thereof using transgenic fermentation methods.

III. Poly-4-hydroxybutyrate Fibers with Prolonged Strength Retention

Around 1984, as division of Johnson and Johnson (Ethicon) first introduced a monofilament synthetic absorbable suture known as PDS™, made from polydioxanone. This suture retains about 50% of its strength up to 6 weeks after implantation, and is completely absorbed in the body within 6 months. Davis and Geck subsequently introduced a monofilament suture based on a copolymer of glycolide and trimethylene carbonate that is sold under the tradename of Maxon™. This suture has a similar strength retention to PDS™. Two other monofilament sutures were introduced more recently. Monocryl™ based on segmented copolymers of glycolide and caprolactone, and Biosyn™ based on a terpolymer of glycolide, p-dioxanone, and trimethylene carbonate. Monocryl™ is reported to have a 20-30% breaking strength after 2-3 weeks, and be completely absorbed after 3-4 months Biosyn™ has an absorption profile similar to Monocryl™. Despite continued innovation in the development of absorbable synthetic monofilament sutures there is, still a need for a synthetic absorbable suture with extended strength retention for patients requiring long-term wound support, for example, a monofilament suture with 50% strength retention at 3-6 months (after implantation). There are also limited options for synthetic absorbable meshes with prolonged strength retention.

U.S. Pat. No. 6,548,569 to Williams et al. discloses that poly-4-hydroxybutyrate has a slower absorption rate in vivo than many materials used as absorbable sutures, and provides absorption data for unoriented poly-4-hydroxybutyrate films and porous samples. It does not, however, disclose the strength retention of fibers of poly-4-hydroxybutyrate following implantation.

It has now been discovered that oriented fibers of PHA4400 and copolymers thereof can be prepared with tensile strengths comparable to existing synthetic absorbable suture fibers (such as PDS™), but have a prolonged strength retention in vivo of over 20-30% at 1-6 months. In comparison, a control PDS suture had little tensile strength remaining after 12-15 weeks.

It has also been discovered that oriented poly-4-hydroxybutyrate fibers can be used to prepare surgical meshes and tubes with prolonged strength retention. These fiber and textile devices may further be combined with autologous, allogenic and/or xenogenic tissues to impart improved properties to these implantable tissues. Properties that can be improved through this combination include mechanical properties such as tensile strength and modulus, for example, to reinforce the tissues to make them stronger, stiffer, more durable, and easier to implant.

Non-limiting examples are given herein to describe the methods for preparing the fibers, meshes, and composite devices with autologous, allogenic and/or xenogenic tissues, and to illustrate the strength retention of the fibers upon implantation.

Example 1: Melt Extrusion of PHA4400 to Produce Monofilament Fibers

PHA4400 (Tepha, Inc., Cambridge, Mass.) (Mw 575K) was ground into small pieces using a Fritsch cutting mill (Pulversette 15, 10 mm bottom sieve) and dried under vacuum overnight prior to melt processing. Monofilament fibers of PHA4400 were melt extruded using an AJA (Alex James Associates, Greer, S.C.) ¾" single screw extruder (24:1 L:D, 3:1 compression) equipped with a Zenith type metering pump (0.16 cc/rev) and a die with a single hole spinnerette (0.026", 2:1 L:D). The 4 heating zones of the extruder were set at 140°, 190°, 200° and 205° C. The extruder was set up with a 15 ft drop zone, 48" air quench zone (10° C.), a guide roll, three winders and a pickup. The fiber was oriented in-line with extrusion by drawing it in a multi-stage process to provide fiber with high tensile strength and a reduced extension to break. The fiber was drawn in-line to stretch ratios of 6 to 11×. A spin finish (Goulston, Lurol PT-6A) was dissolved in iso-propanol at 10 vol/vol % and applied to the fiber before the first roll to act as a lubricant and protect the fiber during downstream processing. A series of fibers of different sizes were produced by varying the extrusion conditions (metering pump speed) and drawing conditions (draw ratio). Tensile mechanical properties of the melt extruded fibers were determined using a universal mechanical tester, and results are shown in Table 1. As is evident, the tensile strength of the oriented PHA4400 fiber is comparable to 450-560 MPa reported for the commercial suture fiber, PDS™, Chu, C. C., et al. *Wound Closure Biomaterials and Devices*, CRC Press (1997). The weight average molecular weight (Mw) of the fibers was determined by gel permeation chromatography (GPC) and is also shown in Table 1.

TABLE 1

Properties of melt extruded PHA4400 monofilament.

| Sample | Draw Ratio | Diameter (μm) | Load at break (g) | Tensile Strength (MPa) | Elongation to Break (%) | Mw** (K) |
|---|---|---|---|---|---|---|
| 1 | 5.95 | 125 | 533 | 426 | 107 | 338 |
| 2 | 5.95 | 113 | 274 | 268 | 126 | 293 |
| 3 | 5.95 | 82 | 68 | 126 | 34 | 278 |
| 4 | 5.95 | 128 | 389 | 297 | 134 | 302 |
| 5 | 6.00 | 134 | 426 | 296 | 118 | 313 |
| 6 | 10.75 | 120 | 569 | 494 | 32 | 348 |
| 7 | 10.75 | 120 | 446 | 387 | 29 | 356 |
| 10* | 10.75 | 217 | 1304 | 346 | 70 | 395 |
| 11* | 5.95 | 190 | 1291 | 447 | 135 | 396 |

*Note:
Samples 10 and 11 were spun through a larger spinnerette (0.045", 2:1 L:D).
**Note
Mw of starting polymer was 575K.

Example 2: Strength Retention and Biocompatibility of PHA4400 Monofilament Fibers An implantation study to determine the strength retention of PHA4400 fibers was undertaken in a rabbit model. Sample 10 (shown in Table 1) was selected for these studies because the fiber had an elongation to break of 70% and tensile strength of 346 MPa (60,000 psi) that is comparable to commercial monofilament absorbable sutures. Prior to implantation the fiber was sterilized using cold ethylene oxide gas (40° C., ethylene oxide pressure of 13.7 INHGA, humidity of 1.7 INHGA, dwell time 4 hr, and aeration time 10 hr). A small amount of fiber shrinkage (2%) was noted to result daring the sterilization process. A commercial monofilament absorbable suture material, PDS™, was used as a control.

Under sterile conditions, the sterilized sutures were placed perpendicular to the dorsal midline of the rabbit. After making a small incision, a large hemostat was introduced through the incision into the subcutaneous tissue and tunneled approximately 9 inches into the subcutis layer. The PHA4400 and control (3/0 PDS™) suture fibers were threaded individually through separate surgically created implant area and left in place. The incisions were closed with tissue glue. A total of four test and four control samples were implanted in each rabbit. Animals were maintained for periods of 1, 4, 8, 12, 16 and 26 weeks (2 rabbits per time point) and were observed daily to ensure proper healing of the implant sites. At the end of the appropriate time points, the animals were weighed and euthanized by an injectable barbituate. Tissue sections containing the implanted sutures were excised from the animals. One test and one control sample were fixed in formalin and retained for histological analysis of the tissue surrounding the suture implants. The remaining three samples from each group were cleaned of tissue, wrapped in sterile, saline soaked gauze and returned on the day of explantation for further analysis. Suture samples were further cleaned of residual tissue and dried.

In parallel with the in vivo degradation study, an in vitro degradation study was conducted to generate comparative data. Sterilized PHA4400 monofilament fibers, identical with those used in the implantation study, were incubated in Dulbeco's phosphate buffered saline (pH 7.4, 37° C.) containing sodium azide (0.05%) as a preservative. Six control PHA4400 sutures per time point were enclosed in sterile polyethylene sample bags and removed at the same time as each of the implant samples. The in vivo and in vitro samples were processed identically.

Strength Retention

Figure 3:
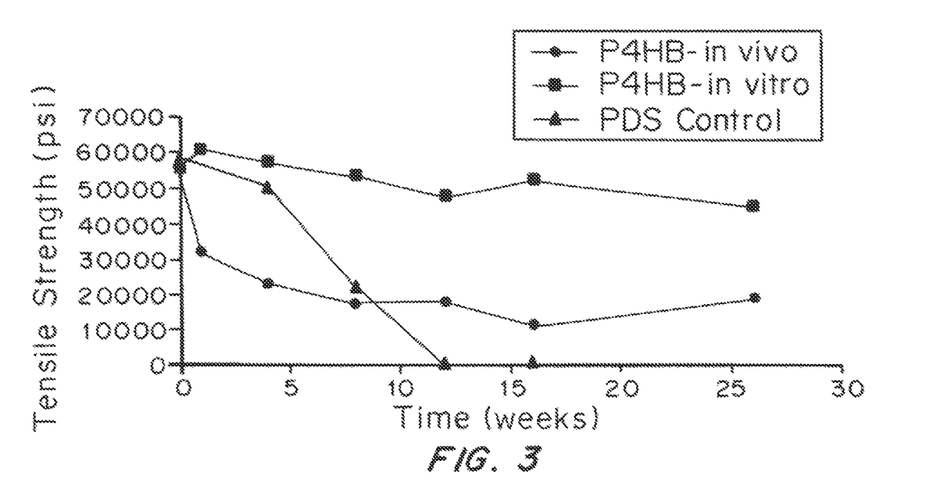
FIG. 3 is a graph of strength retention data of PHA4400 fibers (in vitro and in vivo) compared with PDS control fiber (in vivo).
Figure 4:
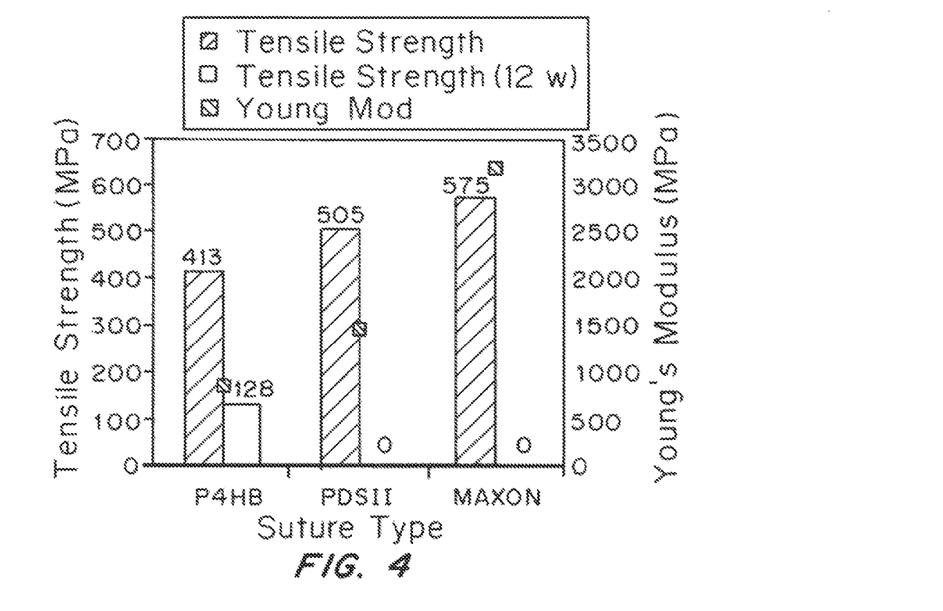
FIG. 4 is a graph comparing the tensile mechanical properties of PHA4400 and commercially available monofilament sutures.

The explained suture samples were subject to tensile testing according to the procedure of ASTM D2256-97. The results of this tensile testing are shown in FIG. 3. As can be seen, the PHA4400 and PDS™ control sutures had very comparable starting tensile strengths (60,000 psi). As expected, the PDS™ control sutures maintained 50% of their initial tensile strength until approximately the $6^{th}$ week. In contrast, the implanted PHA4400 sutures retained approximately 30% of their tensile strength through the $26^{th}$ week. A comparison of the tensile, mechanical properties of PHA4400 and commercially available monofilament sutures is shown in FIG. 4.

Unlike the implanted suture, the PHA4400 in vitro control suture showed a more gradual loss of strength during the entire 26-week degradation study retaining 80% of its original strength. This result demonstrates the mechanical stability of the polymeric material to simple hydrolysis.

Molecular Weight and Mass Loss

Figure 5:
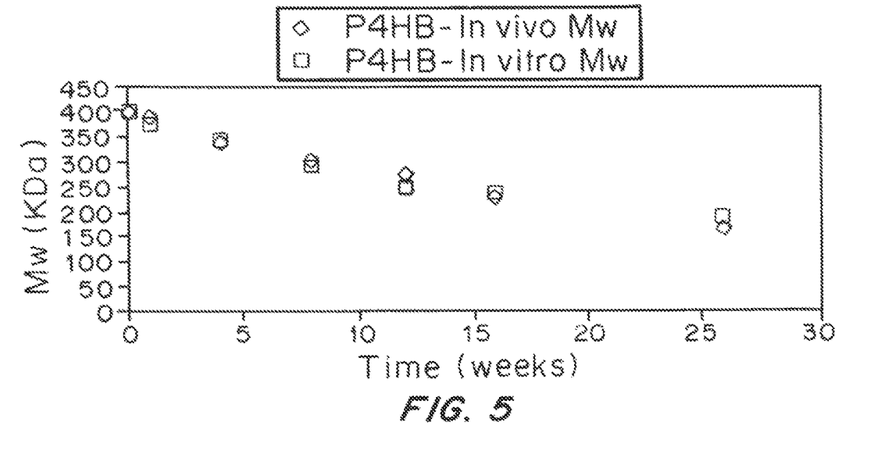
FIG. 5 is a graph of the degradation of PRA4400 (P4HB) samples in vivo compared to in vitro controls. The Mw for implanted (in vivo) and buffer control sutures (in vitro) is plotted versus time.

In addition to the strength retention of the PHA4400 suture fibers, the Mw of the PHA4400 samples were analyzed by GPC. As shown in FIG. 5, the Mw of the implanted and control PHA4400 sutures decreased gradually during the course of the degradation study to approximately 43% of their original Mw at 26 weeks. Additionally, there does not appear to be a significant difference between the Mw of the implanted and the in vitro control PHA4400 sutures. This result shows that the hydrolytic stability of the implanted sample is very similar to the in vitro control.

Figure 6:
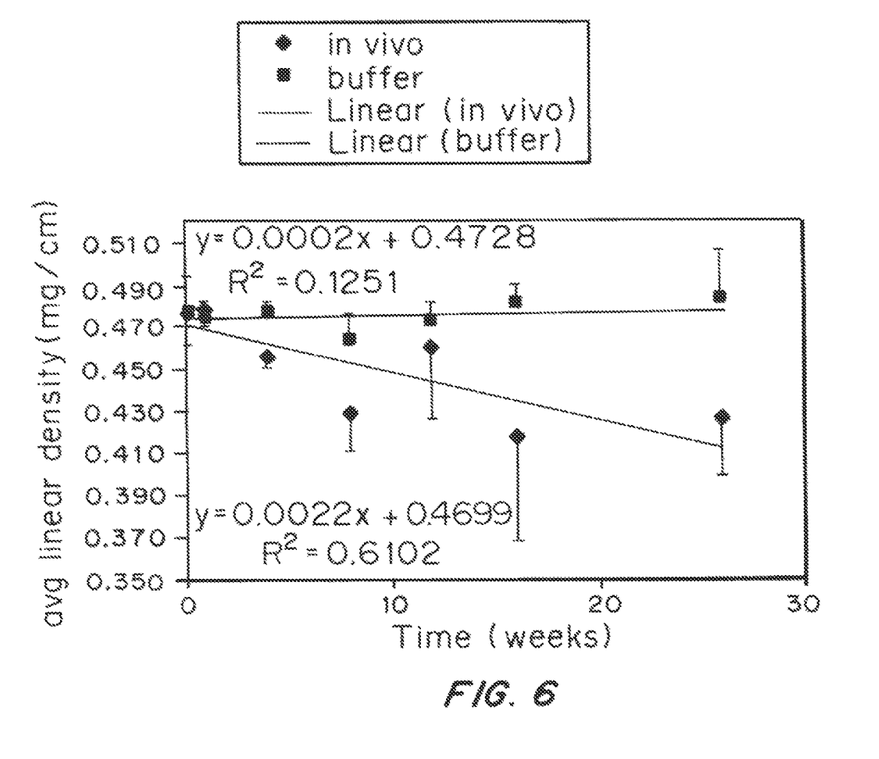
FIG. 6 is a graph of the ratio of mass and length of the PHA4400 sutures (in vitro and in vivo) plotted as a function of degradation time.

In order to determine the mass loss of the samples over time, the mass and length of the PHA4400 sutures (in vitro and in vivo) were determined and plotted as a function of degradation time. The ratio of mass to length of the PHA4400 samples (implanted and buffer control) is plotted vs. degradation time and shown in FIG. 6. The mass/length ratio was determined rather than just the mass of the sample, because this ratio normalizes for samples that were cut during implantation or that break during harvest. As can be seen in this figure, the implanted sutures appear to loose mass more rapidly than the in vitro controls. This data shows that the implanted samples lost mass more rapidly than the in vitro control samples and suggests that surface degradation is occurring in vivo.

Tissue Reaction

The tissue surrounding the implanted PHA4400 and PDS™ control sutures was analyzed for the tissue reaction to the implanted articles through the 26-week time point. Formalin fixed tissue samples (PHA4400 and PDS™ control) from each test animal were sectioned and graded by a board certified veterinarian for the following: inflammation, fibrosis, hemorrhage, necrosis, degeneration, foreign debris and relative size of involved area.

Hisotopathological evaluation indicated that the finding at the PDS™ control and PHA4400 sites were similar and there were no significant indications of a local toxic effect in either the control or the test sites.

Example 3: Knitted Mesh of PHA4400 Monofilament Fibers with Prolonged Strength Retention A warp knitted mesh of PHA4400 was produced from 100 μm diameter oriented monofilament PHA4400 fiber produced as described in Example 1. A warp knit type of construction is desirable as an implant because it can be cut by the surgeon and will not readily unravel. The mesh was fabricated using fiber of 100 μm monofilament PHA4400, tensile strength 92,000 psi, and an elongation to break of 77%. Fabric construction was as follows: Mach #30 Raschel Knit 36 gauge fabric, 150 ends, 16 courses, 40 stitches per inch, using 18 needles per inch. Specifications for the finished fabric were: Weight; 58 g/m² (1.72 oz/sq. yard), Thickness: 0.29 mm.

Example 4: Extrusion of Suture Fibers of a Copolymer of Glycolate and 4-hydroxybutyrate (PHA4422)

PHA4422 containing 5% glycolic acid comonomer (Mw 305,000 by GPC) was melt extruded into a fiber and converted to a suture as follows. The polymer was prepared by milling the bulk polymer into approximately 1 mm sized particles using a P-15 laboratory cutting mill (Fritsch, Germany) dried in a vacuum desicator. The polymer was extruded using an AJA ⅝" single screw extruder (Alex James and Associates) with a single-hole spinneret (0.040", 2:1 L/D). The extruder had five separate temperature zones that were set to 120, 154, 155, 160 and 160° C. from the inlet to the outlet, with a gear pump at the outlet. The total residence time in the extruder was estimated at 9 minutes. After extrusion there was a 10 ft drop zone through air before a quenching water bath (5° C.). Following the quench bath, three winders were used to collect the fiber. A first winder was set for a speed of about 2.5 meters per minute. The bath length was about 3-4 ft and the residence time for the fiber in the bath was estimated at about 30 seconds. Crystallization of the fiber occurred before the first winder. Two additional winders (17.5 and 19.5 meters/minute) extended the fiber about 8 times (8× draw). A take up unit was used with only slight tension. Varying the polymer extrusion rate while keeping the downstream orientation and take up rates the same produced fibers of different diameters. Initially, the extruder was set at a gear pump rate of 7, and then successively slowed resulting in fibers of approximately 375, 275 and 200 μm diameter, see Table 2.

Suture needles were attached to each of the different diameter fibers and the sutures were packaged for sterilization. Tensile strength (straight and knot pull) was determined for representative samples of the sutures, see Table 2.

TABLE 2

Physical characterization of sutures prepared by melt extrusion of PHA4422 (5% glycolic acid comonomer, Mw 300K).

| Fiber diameter (μm) | Corresponding USP size approx. | Tensile Strength Straight Pull (lbf) | Elongation Straight Pull (%) | Tensile Strength Knot Pull (lbf) | Elongation Knot Pull (in) |
|---|---|---|---|---|---|
| 375 +/− 6 | 0   | 9.2 +/− 1.6 | 128 +/− 33 | 4.6 +/− 0.4 | 51 +/− 4.2 |
| 256 +/− 2 | 2/0 | 5.3 +/− 0.3 | 65 +/− 13  | 3.8 +/− 0.8 | 49 +/− 18  |
| 199 +/− 5 | 4/0 | 3.0 +/− 0.3 | 130 +/− 24 | 1.6 +/− 0.3 | 44 +/− 15  |

Example 5: Monofilament Fiber with Peak Tensile Stress of Greater that 70 kg/mm$^2$ Melt spinning of Poly-4-hydroxybutyrate "PHA4400" polymer has been extremely difficult to accomplish due to melt flow instability and tackiness of resulting fiber. Melt leaving the spinning die exhibited periodic diameter fluctuation and helical structure. These flow irregularities are known as melt fracture or "elastic turbulence" and are generated while the melt is entering and passing through spinneret hole. The reason for such flow irregularities is very high viscosity of the viscoelastic melt and a very high elastic function at the exiting point of spinneret capillary.

The low glass transition temperature of about −50° C., and the low tendency to crystallize of this polymer explain the stickiness of the fibers. In addition to that, the orientation, which was generated during melt spinning, relaxed after a very short time so that the fibers offered a low tenacity for further drawing.

This example illustrates our ability to overcome the above processing problems and produce high strength fiber. PHA4400 polymer was dried to less than 0.01% moisture. Dried pellets of the PHA4400 were fed to an extruder barrel under a blanket of nitrogen. Barrel temperatures zones were kept at 100° C. feed, 150° C. transition and 200° C. metering. Molten polymer passed through a heated block to a metering pump then extruded from a die with a single hole spinneret. The block, metering pump and the die were kept at 220° C. temperature. Pump discharge pressure was kept below 1000 psi by control of temperatures, and the speed of the metering pump. Spun extrudate filament was free from all melt irregularities. The extrudate was allowed dwell time to crystallize after which further multi stage drawing was possible to increase crystal orientation and gain strength. The fiber was then heat treated and rolled on a winding spool. Properties of the ensuing fiber are shown in Table 3.

TABLE 3

Physical characterization of fibers prepared by melt spinning of PHA4400

| Fiber Min Diam. microns | Fiber Max. Diam. microns | Peak Load kgf | Min Break Strength kgf/mm$^2$ | Min Break Strength PSI | Min Break Strength MPa |
|---|---|---|---|---|---|
| 0.070 | 0.089 | 0.46  | 73.98 | 1.05E+05 | 726 |
| 0.129 | 0.178 | 1.80  | 72.37 | 1.03E+05 | 710 |
| 0.256 | 0.305 | 5.50  | 75.32 | 1.07E+05 | 739 |
| 0.421 | 0.470 | 13.00 | 74.97 | 1.07E+05 | 735 |
| 0.523 | 0.622 | 22.70 | 74.74 | 1.06E+05 | 733 |

"Diam" means Diameter

Example 6: Monofilament Fibers with Prolonged In Vivo Strength Retention

The PHA4400 monofilaments prepared as in Example 5 were sterilized using cold ethylene oxide gas (40° C., ethylene oxide pressure of 13.7 INHGA, humidity of 1.7 INHGA, well time 4 hr, and aeration time 10 hr).

Under sterile conditions, the sterilized monofilament fibers were placed perpendicular to the dorsal midline of the rabbit. After making a small incision, a large hemostat was introduced through the incision into the subcutaneous tissue and tunneled approximately 9 inches into the subcutis layer. The PHA4400 fibers were threaded individually through separate surgically created implant areas and left in place. A total of four test and four control samples were implanted in each rabbit. Animals were maintained for a period of 2 weeks (2 rabbits) and were observed daily to ensure proper healing of the implant sites. At the end of the appropriate time points, the animals were weighed and euthanized. Tissue sections containing the implanted sutures were excised from the animals. Samples were cleaned of tissue, wrapped in sterile, saline soaked gauze and returned on the day of explantation for further analysis. Suture samples were further cleaned of residual tissue and dried. Tensile strength was determined on a universal testing machine. The tensile breaking load of the explanted fiber after 2 weeks implantation was found to be 8.5 lbf peak load, which is 87% of that of the starting fiber (9.8 lbf). Thus these fibers demonstrated a higher strength retention in vivo (87% at 2 weeks) when compared to the fibers in Example 2, FIG. 3 (50% at 2 weeks).

Example 7: Multifilament Yarn

Fiber spinning was carried out in the same manner as example 5 except with the die having a multi hole spinneret (20 holes×0.0065 inches). Extrudate yarn was allowed time to crystallize, and a super cooled stream of gaseous media/liquid mist perpendicular to the fiber axis was introduced. A subzero bath was also used and proved a suitable substitute for the gaseous media. The resulting filaments were further processed through cold and heated godets, and the filaments could be oriented and heat set. Yarn tenacity of greater than 3.5 gpd (gram per denier) with 30% elongation was obtained. Representative data for the multifilament yarns is shown in Table 4.

TABLE 4

Tensile properties for PHA4400 multifilament yarns.

| Sample | Denier per filament | Peak Load Kg | Strain at break (%) | Tenacity g/denier |
|---|---|---|---|---|
| 1 | 33.8 | 2.43 | 97  | 3.6 |
| 2 | 27.1 | 1.69 | 114 | 3.1 |
| 3 | 23.7 | 1.92 | 58  | 4.1 |
| 4 | 16.2 | 1.12 | 113 | 3.4 |
| 5 | 12.8 | 0.99 | 107 | 3.9 |
| 6 | 10.3 | 0.71 | 74  | 3.5 |

Example 8: Knitted Fabric from a Multifilament Yarn

A multifilament yarn was knitted into a tube using, a single feed, circular weft knitting machine (Lamb Knitting Co., model ST3A/ZA). The width of the flat tube was approximately 9 mm. The yarn knitted very well without evidence of fiber breakage even without the addition of a spin finish as a lubricant. After cleaning and sterilization, the knitted tube appears well suited for use as an absorbable medical fabric.

Example 9: Absorbable Polymeric Support Structure for Biological Tissue Implant

PHA4400 fiber woven, knitted or braided into semi rigid support tubes or PHA400 polymer directly extruded into support tubes can be prepared with an inner diameter closely matching that of a biological substrate implant (e.g. autologous, allogenic and/or xenogenic tissue). The biological implant can be inserted into the support tube, and may optionally be secured in place, for example, by suturing, prior to implantation. The addition of the support tube provides improved strength, modulus, and can make implantation easier. Similarly sheets of extruded film, woven, non-woven or knitted fabric may be rolled over a biological tissue implant and the fabric ends may be tied, sutured or glued to maintain a semi-rigid construct over the biological implant.

A woven tube was produced from 0.300 mm diameter monofilament PHA4400 fiber extruded as described in Example 5. Using circular weaving equipment a 10 mm inside diameter tube was produced. The tube construction allowed insertion of an implant biological substrate and provided enough stiffness to position and suture an otherwise flaccid biological implant.

We claim:

1. A knitted mesh, woven mesh, nonwoven mesh or braid comprising a poly-hydroxybutyrate homopolymer multifilament yarn, wherein the multifilament yarn has a tenacity of greater than 0.5 g/denier and is produced by a method comprising melt extrusion, allowing the extrudate dwell time to crystallize and drawing the resulting fiber.

2. The knitted mesh, woven mesh, nonwoven mesh or braid of claim 1 wherein the yarn has been oriented.

3. The knitted mesh, woven mesh, nonwoven mesh or braid of claim 1 further comprising a monofilament of poly-4-hydroxybutyrate polymer.

4. The knitted mesh, woven mesh, nonwoven mesh or braid of claim 1 wherein the elongation to break of the multifilament yarn is between 30% and 114%.

5. The knitted mesh, woven mesh, nonwoven mesh or braid of claim 1 wherein the multifilament yarn is produced by a method that comprises spinning the multifilament at a temperature that is greater than the glass transition temperature of the polymer, optionally, wherein the method comprises heating at a temperature greater than 150° C., and stretching the multifilament at a temperature above the polymer's glass transition temperature while allowing the polymer time to crystallize.

6. A medical device comprising the knitted mesh, woven mesh, nonwoven mesh, or braid of claim 1.

7. The medical device of claim 6 wherein the knitted mesh, woven mesh, nonwoven mesh or braid is combined with harvested autologous, allogeneic and/or xenogeneic tissue.

8. The devices of claim 6, where the device is selected from the group consisting of a tube, general surgical mesh, hernia mesh, suture, pericardial patch, anti-adhesion patch, cardiovascular patch, guided tissue regeneration patch, sling, braid, ligament or tendon repair device, meniscus repair device, cartilage repair device, nerve guide, stent, vascular graft, dural patch, organ salvage device, intracardiac defect closure device, mastopexy/breast reconstruction device, tracheal reconstruction device, and bladder repair device.

9. A method of using the device of claim 8, the method comprising the steps of implanting the device in a patient for pelvic floor reconstruction, urethral suspension, hernia repair, suturing, pericardial repair, cardiovascular patching, cardiac support, myocardial regeneration, organ salvage, elevation of the small bowel during radiation of the colon in colorectal cancer patients, bone, cartilage, and meniscus grafting procedures, guided tissue regeneration, vascular grafting, dural substitution, nerve repair, prevention of adhesions, ligament and tendon repair, mastopexy/breast reconstruction, vascular grafts/fistulae, GI (gastro intestinal) resection, tracheal reconstruction, intracardiac defect closure, support is disc herniation palliation, urinary bladder repair, and encephalocele/meningomyelocele repair.

10. The knitted mesh, woven mesh, nonwoven mesh or braid comprising a multifilament yarn of claim 1 wherein the multifilament yarn has a tenacity between 0.5 g/denier and 4.1 g/denier.

11. The knitted mesh, woven mesh, nonwoven mesh or braid comprising a multifilament yarn of claim 1 wherein the multifilament yarn has a tenacity between 3.1 g/denier and 4.1 g/denier.

* * * * *

UNITED STATES PATENT AND TRADEMARK OFFICE
CERTIFICATE OF CORRECTION

PATENT NO. : 10,136,982 B2
APPLICATION NO. : 14/276693
DATED : November 27, 2018
INVENTOR(S) : David P. Martin et al.

Page 1 of 1

It is certified that error appears in the above-identified patent and that said Letters Patent is hereby corrected as shown below:

In the Specification

Column 1, Line 59, replace "Master Files" with --Master File--.
Column 3, Line 5, replace "leave as" with --leave a--.
Column 3, Line 24, replace "front" with --from--.
Column 3, Line 39, replace "risk the disease" with --risk for disease--.
Column 4, Line 4, replace "unproved" with --improved--.
Column 4, Line 22, replace "PRA4400" with --PHA4400--.
Column 4, Line 66, replace "as division" with --a division--.
Column 5, Line 14, replace "3-4 months" with --3-4 months.--.
Column 5, Line 16, replace "there is," with --there is--.
Column 6, Line 54, replace "daring" with --during--.
Column 6, Line 64, replace "area" with --areas--.
Column 7, Line 23, replace "explained" with --explanted--.
Column 7, Line 32, replace "tensile," with --tensile--.
Column 7, Line 60, replace "loose" with --lose--.
Column 9, Line 39, replace "temperatures" with --temperature--.
Column 10, Line 7, replace "well" with --dwell--.

In the Claims

Claim 1, Column 11, Line 32, replace "poly-hydroxybutyrate" with --poly-4-hydroxybutyrate--.
Claim 9, Column 12, Line 36, replace "support is" with --support in--.

Signed and Sealed this
Twenty-first Day of May, 2019

Andrei Iancu
*Director of the United States Patent and Trademark Office*